US00PP08846P

United States Patent [19]

Weeks

[11] Patent Number: Plant 8,846

[45] Date of Patent: Jul. 26, 1994

[54] HYBRID TEA ROSE PLANT NAMED 'PAUL HARRIS'

[75] Inventor: O. L. Weeks, Chino, Calif.

[73] Assignee: Estrella Rose Company, Litchfield Park, Ariz.

[21] Appl. No.: 811,985

[22] Filed: Dec. 23, 1991

[51] Int. Cl.[5] ..... A01H 5/00

[52] U.S. Cl. ..... Plt./15

[58] Field of Search ..... Plt. 15, 11, 22, 24

*Primary Examiner*—Howard J. Locker

*Attorney, Agent, or Firm*—Joseph H. Roediger

[57] ABSTRACT

A new and distinct of Hybrid Tea rose plant is provided having double flowers of original yellow blend with outer edge of bloom petals tinged with reddish splotches. The average stem length is 15 to 18 inches. The new variety is particularly suited for use in the beautification of parks and gardens.

1 Drawing Sheet

BACKGROUND OF THE NEW PLANT

The present invention relates to a new and distinct variety of rose plant of the hybrid tea class which is distinguished from already known varieties in this class and color range. The new variety of rose plant was originated by me by crossing the variety Summer Sunshine U.S. Plant Pat. No. 2,078 with the variety Georgia U.S. Plant Pat. No. 4,712 to produce the female parent (seed parent). The male or pollen parent is an unnamed proprietary seedling maintained under my direction. The new variety is the product of the pollination of the above-noted seed-parent and pollen parent.

Among the novel characteristics possessed by this new variety are the double flower of Medium Yellow blend tinged at its outer edge with reddish splotches. The flower is even in its yellow color and fade resistant. The plant has an erect growth habit which is well organized and balanced. In addition, the plant tolerates heat conditions very well. Because of the above-mentioned characteristics, the present invention responds to the needs of the horticultural industry for all uses and, particularly, for park and garden decoration.

This new variety of rose plant owes its origin to an artificial pollination made between the two parents by me in a greenhouse in Chino, Calif. and is expressed as follows: (Summer Sunshine × Georgia) × unnamed seedling. The seeds resulting from the above-noted pollination were sown and small plants were obtained. These plants were both physically and biologically distinct one from the other. After eliminating all of the deficient or abnormal subjects whose characteristics deviated from those which were the object of my research, propagation of the remaining plants was undertaken. In the course of this study, all the varieties were systematically eliminated save one, the one closest to the desired goal.

Technical tests including propagation by budding, grafting and cuttage were then undertaken in a greenhouse in Chino, Calif. with the aim of verifying the behavior and the productiveness of the created variety. The results were conclusive and stressed the importance of this variety with a view to its exploitation for all use and, most particularly, for park and garden decoration.

The characteristics and properties of the new variety obtained are stable and are tranmissible by budding, grafting and cuttage through succeeding propagations.

This new variety is called the Paul Harris variety of hybrid tea rose plant.

DESCRIPTION OF THE DRAWING

The accompanying drawing shows in colors as nearly true as it is reasonably possible to attain in color photographs of this nature: canes with thorns, terminal growth, the flower in various stages of maturity, detached petals and foliage of the new plant.

DESCRIPTION OF THE NEW VARIETY

The following descriptive characteristics of the new variety were taken from two (2) year old plants grown in container in the greenhouse in Chino, Calif. and observed during the month of April.

The *Pantone Library of Color*, 1990 edition is used for the identification of the colors. The terminology which precedes the numbered references proper to this chart has been added to qualify, in common terms, corresponding colors.

THE PLANT

Class: Hybrid tea.

Height: 42–44 inches.

Habit: Upright.

Branches:

*Young stems.*—Pantone 376C green group.

*Adult wood.*—Pantone 384C yellow group.

*Thorns.*—Size: Medium. Quantity: Moderately numerous. Color: Young stems: Red Pantone 194C. Adult stems: Brown Pantone 499U.

Leaves:

*Stipules.*—Adnate, pectinate, wide and dented.

*Petioles.*—Upper side: Young leaf — light green. Adult leaf — medium green. Under side: Medium green, smooth.

*Leaflets.*—Number: 3, 5 and 7. Sometimes the lower pair of leaflets is incomplete. Shape: Oval, based round to obtuse. Serration: Single and regular. Texture: Consistent. General effect: Dense, medium green. Color — Young foliage: Upper side: Pantone 362C. Under side: Pantone 578U with reddish stain. Color — Adult foliage: Upper side: Pantone 364C. Under side: Pantone 377U.

Inflorescence:

*Number of flowers.*—Usually 1 flower per stem.

*Stem length.*—15 to 18 inches.

*Peduncle.*—Length is 2½ inches average, heavy caliper.

*Sepals.*—Upper side: Greenish, tomentose. Shape: Simple and do not extend beyond the bud.

*Bud.*—Shape: Pointed. Length: 1¼ inches. Size: Medium to large, ovoid to urn shaped. Color: As the calyx breaks, the petals are overlaid with slight tinge of Pantone Warm Red U on outer edge. Upper side: Pantone 108U. Under side: Pantone 107U.

Flower:

*Shape.*—Cuplike, well shaped, high center. Then as flower matures cuplike shape tend to flatten as petals enlarge and spread outwardly.

*Diameter.*—4 to 4½ inches.

*Color.*—When opening: Upper side: Pantone 113U. Under side: Pantone 120U. Outer edge: Tinged with Pantone Warm Red U. When blooming: Upper side: Pantone 107U. Under side: Pantone 106U. Outer edge: Tinged with Pantone Warm Red U. When finishing bloom: Upper side: Pantone 102U. Under side: Pantone 101U. Outer edge: Tinged with Pantone Warm Red U. Petal coloration: Near point of attachment: Pantone 113U. At point of attachment: Pantone 108U.

*Bloom range.*—Flowers last 5-7 days on plant. As a cut flower, at room temperature, 6-9 days.

*Fragance.*—None.

*Lasting Quality.*—Long Lasting.

*Petals.*—Shape: Obovate through flower maturity, enlarging with bloom cycle. Outer petals are obovate; inner petals are obovate with rounded apex. Texture: Consistent, velvety. Number: 30 on average. Cleaning: Good.

*Stamens.*—Number: About 150. Anthers: Normal strawlike. Filaments: Irregular in height, bright yellow at base turning orange the orange-red near filaments. Uniformly located around receptacle.

*Pistils.*—Number: About 52 outside — 45-50 bundled together inside. Stigmas: Normal, ochre colored. Style: Uneven length from 0.118 to 0.552 inches (3 to 14 mm).

*Receptacle: Medium green, smooth, wide, pitcher shaped.*

Development:

*Vegetation.*—Vigorous.

*Blooming.*—Continuous throughout seasons.

*Aptitude to bear fruits.*—Moderate.

*Resistance to frost.*—Good.

*Resistance to diseases.*—Normal.

I claim:

1. A new and distinct variety of Hybrid Tea rose plant named Paul Harris as described and illustrated.

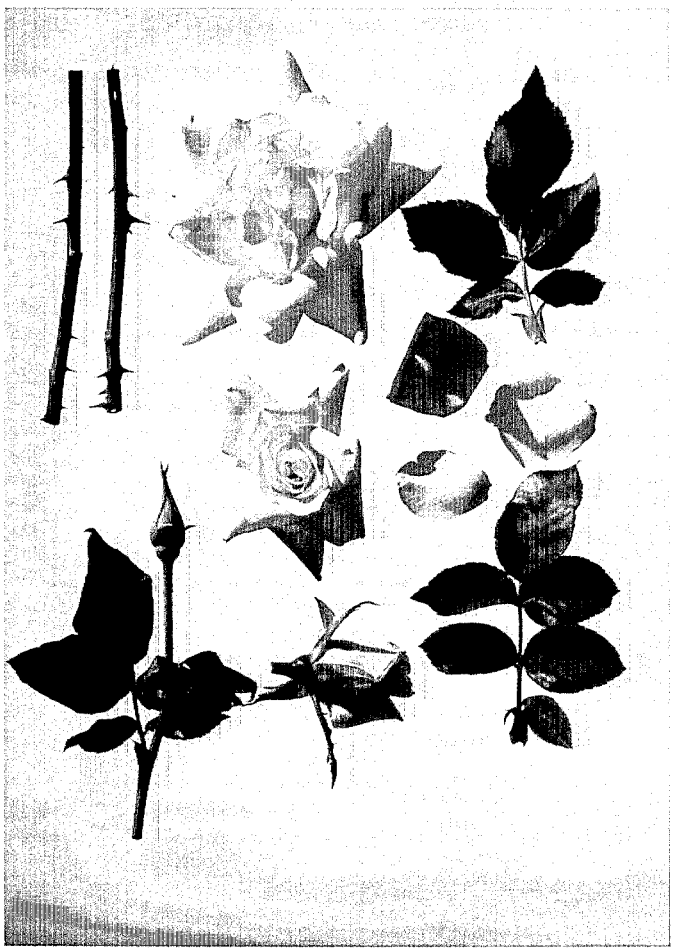

* * * * *